United States Patent [19]

Nakatani et al.

[11] 4,450,097

[45] May 22, 1984

[54] ANTIOXIDATIVE COMPOUND, METHOD OF EXTRACTING SAME FROM ROSEMARY, AND USE OF SAME

[75] Inventors: Nobuji Nakatani, Tokyo; Reiko Inatani, Osaka; Tadashi Konishi, Kanagawa, all of Japan

[73] Assignee: Lion Corporation, Tokyo, Japan

[21] Appl. No.: 351,631

[22] Filed: Feb. 23, 1982

[30] Foreign Application Priority Data

Feb. 26, 1981 [JP] Japan ................................ 56-27434
Mar. 29, 1981 [JP] Japan ................................ 56-45783

[51] Int. Cl.³ ..................... C09K 15/08; C09K 15/34; A23L 1/28
[52] U.S. Cl. .................................. 252/404; 252/398; 426/429; 426/654; 426/655; 549/298
[58] Field of Search ................ 252/404, 398; 426/429, 426/654, 655; 549/298

[56] References Cited

U.S. PATENT DOCUMENTS 3,950,266  4/1976  Chang et al. .................. 426/655 X
3,992,416  11/1976 Bolz et al. .......................... 549/298
4,195,101  3/1980  Saito et al. ...................... 252/404 X
4,380,506  4/1983  Kimura et al. .................... 252/398

Primary Examiner—Benjamin R. Padgett
Assistant Examiner—Matthew A. Thexton
Attorney, Agent, or Firm—Toren, McGeady and Stanger

[57] ABSTRACT

The invention provides a novel antioxidant obtained from rosemary and suitable for preventing oxidation of various organic materials or, in particular, oleaginous foodstuffs. The antioxidant is prepared by extracting rosemary with a non-polar organic solvent and further extracting the thus extracted material with an aqueous alkaline solution having a pH of at least 10.5 as a weakly acidic fraction soluble in such a strongly alkaline solution. The extraction with the non-polar organic solvent is preferably preceded or followed by steam distillation in order to remove any spicy volatile materials undesirable when the antioxidant is added to foodstuffs or the like. Column chromatographic separation of the above obtained weakly acidic fraction into components gives a novel compound 7$\beta$,11,12-trihydroxy-6,10-(epoxymethano)abieta-8,11,13-trien-20-one as the effective ingredient of the antioxidant prepared from rosemary. Characterization of the above novel compound is given.

8 Claims, 5 Drawing Figures

ANTIOXIDATIVE COMPOUND, METHOD OF EXTRACTING SAME FROM ROSEMARY, AND USE OF SAME

BACKGROUND OF THE INVENTION

The present invention relates to a novel compound having antioxidative power and an antioxidant containing the same compound. More particularly, the present invention relates to a novel compound 7β,11,12-trihydroxy-6,10-(epoxymethano)abieta-8,-11,13-trien-20-one and an antioxidant containing the above comound as well as a method for the preparation of the antioxidant from a natural plant.

It is known that several herbal spices have an effect of preventing oxidation of fats and oils or oleaginous foodstuffs when the spices are blended therewith and a large number of papers have been published reporting the results of the investigations on the antioxidative power of these herbal spices. On the other hand, along with increasing consumption of synthetic antioxidants such as butyl hydroxyanisole (BHA) and dibutyl hydroxytoluene (BHT) as an antioxidative additive in oleaginous foodstuffs, it might be a natural consequence that certain decline was noted once in the investigations on the antioxidative effect of the antioxidants of natural origin such as the herbal spices.

On the contrary, recent social concern and interest in the pharmacy and food industry are directed to the problem of safety of synthetic medicines and food additives and re-evaluation of these synthetic materials in this respect is strongly desired. In accordance with this trend, the effectiveness of natural spices as an antioxidant has come into reconsideration and investigations are now again widely undertaken with activity not only from the standpoint of safety but also as a matter of tastiness when used in foodstuffs.

To give a historical overview on the investigations directed to the detection of the antioxidative ingredients in natural spices, it was the first that the effective ingredient named carnosol extracted from sage, a plant belonging to Salvia carnosa Dougl, as the bitter-tasting component thereof was a phenolic ester compound of a molecular formula $C_{19}H_{26}O_4$ containing hydroxyphenanthrene (A. I. White et al., J. Amer. Pharm. Assoc. Sci. Ed., pages 31, 33 and 37, 1942) followed by the report establishing that the above mentioned carnosol is the same compound as picrosalvin which was obtained from sages belonging to the species of Salvia officinalis L. or Salvia triloba L. or rosemary belonging to Rosmarinus officinalis L. as the bitter-tasting component thereof expressed by the following structural formula (C. H. Brieskorn et al., J. Org. Chem., volume 29, page 2293, 1964):

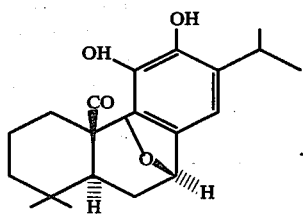

(I)

Further, it was determined that rosemary contains a carnosic acid expressed by the following structural formula as reported by Wenkert et al. (E. Wenkert et al., J. Org. Chem., volume 30, page 2931, 1965) as the main terpenic component therein:

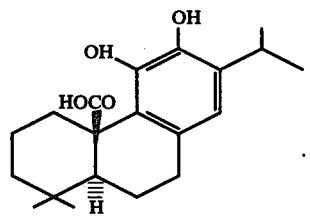

(II)

Recently, it was suggested that, from the results of the high-speed liquid chromatography into the individual ingredients following washing with water and decolorization, the material extracted from rosemary and sage with a solvent contains certain tasteless and odorless compounds having antioxidative power in addition to the carnosic acid, carnosol and ferruginol known as antioxidants (S. S. Chang et al., J. Food. Sci., volume 42, page 1102, 1977).

Notwithstanding a large number of published reports including the above described ones, the detection and identification of the antioxidative ingredients in herbal spices are only at the very beginning stage of the investigations now on the way and many problems are left unsolved.

Apart from the detection and isolation of the antioxidatively effective ingredients from the herbal spices, it is of course a possible way to use the herbal spice as such as an antioxidant in foodstuffs. This way of using the spices as such is, however, applicable not all of the foods of which strong spicy flavor should be avoided as in the Japanese-style foods since the strong characteristic flavor of the spice usually destroys the taste and flavor of the food per se. Therefore, it is very desirable to extract and concentrate the antioxidative ingredient from the spices and to use the thus concentrated antioxidative ingredient as an antioxidant in foodstuffs. In this connection, there has been proposed in Japanese Patent Publication No. 53-9595 that a spice such as rosemary is directly subjected to the extraction with an alkali solution at a pH of 7 to 10 to give a fraction containing the above mentioned carnosic acid which can be used as an antioxidant. It is noted there that the alkali solution as the extractant should have a pH not exceeding 10 because the material extractable with a strong alkali of a pH higher than 10 has an effect of substantially accelerating oxidation.

SUMMARY OF THE INVENTION

The investigations leading to the present invention have been undertaken by the inventors with an object to examine the antioxidative fractions obtained from rosemary and it has been unexpectedly discovered that a very strong antioxidative fraction can be obtained when rosemary is first subjected to an extraction treatment with a non-polar solvent and a scrubbing treatment by steam distillation followed by the extraction with a strong aqueous alkali solution at a pH of 10.5 or higher. This result is rather surprising in view of the teaching in the above recited Japanese patent that extraction of rosemary with a strong alkali solution is undesirable.

Thus, the antioxidant of the present invention is prepared by a method comprising the steps of (a) extracting rosemary with a non-polar organic solvent to give an extract, (b) scrubbing the extract by steam distillation to leave a residue, and (c) subjecting the above residue to an extraction treatment with an aqueous alkali solution at a pH of 10.5 or higher to give an extracted fraction exhibiting strong antioxidative power.

In the above procedure, the order of the steps of (a) and (b) may be reversed. That is, the steam distillation is undertaken first with rosemary as the starting material and then the thus scrubbed rosemary is subjected to the extraction with a non-polar organic solvent to give an extract of which the extraction with an aqueous alkali solution is performed.

The above obtained antioxidative fraction has been further subjected to column chromatography to separate the effective ingredients arriving at a conclusion that the most effective ingredient contained therein is a novel compound named 7β,11,12-trihydroxy-6,10-(epoxymethano)abieta-8,11,13-trien-20-one and expressed by the following structural formula:

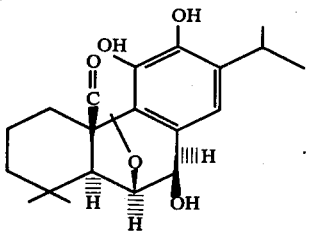

(III)

DETAILED DESCRIPTION OF THE PREFERRED EMBODIMENTS

Figure 1:
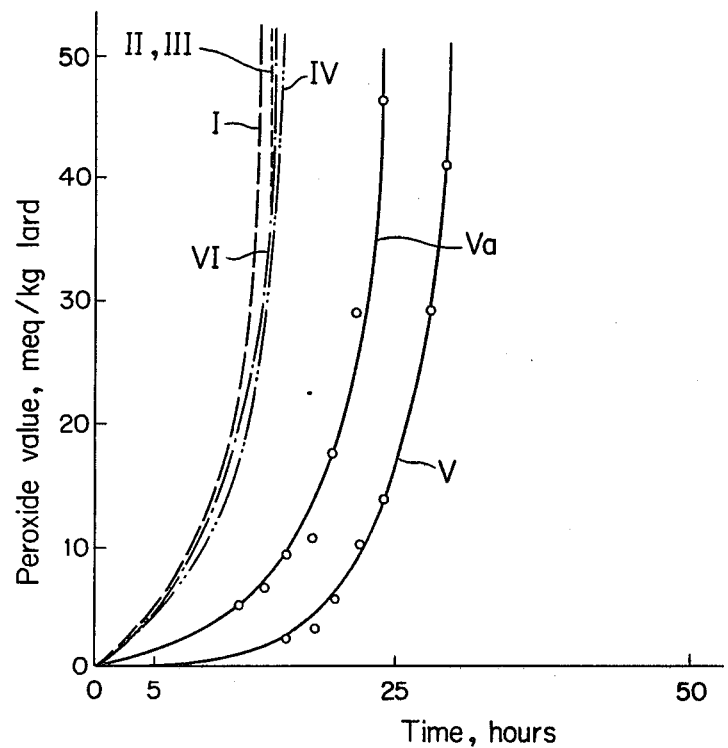
FIG. 1 is a graph showing the antioxidative effect of the fractions extracted from rosemary. See text for the Nos. I to VII indicating the curves.

As is mentioned above, the first step for the preparation of the inventive antioxidant is the solvent extraction or steam distillation of rosemary. Following description is given for the case where the extraction with a non-polar solvent is first undertaken prior to the steam distillation.

The starting material is rosemary which is a plant belonging to the species of Rosmarinus officinalis L. and it is used either as fresh or as dried. Usually, dried leaves of rosemary are used as pulverized. Suitable non-polar solvents for the extraction of rosemary are exemplified by petroleum ether, ligroin, n-hexane, cyclohexane, carbon tetrachloride, chloroform, dichloromethane, chlorinated ethanes, e.g. dichloroethanes, monochloroethane and the like, diethyl ether, benzene, toluene and the like, of which n-hexane and dichloromethane are preferred. They are used either singly or as a mixture of two kinds or more according to need. The amount of the solvent is not particularly limitative but preferably in the range from 3 to 10 parts by weight per each part by weight of the dried rosemary.

The method of extraction may be conventional including a batchwise leaching method and continuous extraction under reflux of the solvent as in the Soxhlet extractor, the latter method being preferred due to the better efficiency. When the extraction is performed by the method of batchwise leaching, the powder of dried rosemary is dispersed in the solvent and, after agitation at room temperature for 2 to 24 hours, the extract solution and the residue are separated, for example, by filtration, decantation or centrifugal separation and the extraction is repeated once to several times with the thus separated residue in the preceding leaching. The extract solutions obtained by repeating the leaching are combined together and the solvent is removed therefrom by distillation under normal pressure or reduced pressure to leave the extracted material in a concentrated form.

The scrubbing treatment by steam distillation is undertaken either with the raw rosemary or with the above obtained extracted material. The procedure of steam distillation is also conventional and the solid material is dispersed in, preferably, 10 times by weight or more of water and heated in water to boiling either under the atmospheric pressure or under a reduced pressure for a time of 0.5 to 10 hours. The flavory components contained in the starting spice are removed by this steam distillation as being dissipated together with the steam. The steam distillation is continued until no smell of the spice is felt in the distillate. Dissipation of the flavory component from the dispersion can be accelerated by blowing steam into the dispersion. After completion of the steam distillation, the solid material is taken from the aqueous dispersion as hot or after cooling by a conventional method of solid-liquid separation such as filtration, decantation or centrifugal separation. When the above steam distillation has been carried out with raw rosemary prior to the extraction with a solvent, the thus obtained solid material after steam distillation is then dried and subjected to the extraction with a solvent in the same manner as described above.

The following step is the extraction of the above obtained solid material with an aqueous alkali solution. Thus, the solid material is dissolved in 1 to 10 times by weight of a non-polar organic solvent and this solution is contacted with an aqueous alkali solution at a pH of 10.5 or higher by a conventional method of liquid-liquid extraction whereby the effective ingredients contained in the solid material extracted from rosemary are transferred into the aqueous phase. The non-polar arganic solvent suitable for dissolving the solid material in this case may be the same as in the extraction of the raw rosemary.

Besides the above described extraction of the solid material with a strong alkali solution at a pH of 10.5 or higher, the solid material can be fractionated into four fractions according to the acidity or basicity of the fractions utilizing the solubility in several aqueous extractants with different concentrations of acid or alkali. For example, the fraction with basicity is obtained by extracting from the organic solution of the solid material with an aqueous solution of hydrochloric or sulfuric acid. The strongly acidic fraction is then extracted from the organic solution depleted of the basic fraction as above, followed by washing with water, with an aqueous solution of a weak alkali such as sodium hydrogencarbonate and further the weakly acidic fraction is obtained from the organic solution washed with water following the above extraction with an aqueous solution of a strong alkali such as sodium hydroxide or potassium hydroxide. Finally, the neutral fraction is obtained from the organic solution washed with water following the above three extractions with acid or alkali when the organic solution is dehydrated with a drying agent such as anhydrous magnesium sulfate or anhydrous sodium sulfate and concentrated by evaporating the solvent.

Meanwhile, no particular difficulties are encountered in separating the basic, strongly acidic and weakly acidic fractions from the aqueous acidic or alkaline extracts obtained in the above described manner. That is, the acidic extract containing the fraction with basicity is alkalified by adding a small amount of an alkali and the alkaline aqueous solution is subjected to extraction with an organic solvent such as diethyl ether followed by the removal of the solvent from the extract solution to give the basic fraction isolated. Similarly, the strongly and wealky acidic fractions are obtained from the respective aqueous alkaline extract solutions by extraction with an organic solvent, e.g. diethyl ether, following acidification with hydrochloric acid or sulfuric acid and followed by removal of the solvent by evaporation.

It should be noted that all of these four fractions as well as the material vaporized in the steam distillation exhibit antioxidative effect more or less although the antioxidative activity of the weakly acidic fraction, i.e. the fraction extracted with the strong alkali solution, is the strongest by far.

To give a more detailed description of the extraction with the strong aqueous alkali solution at a pH of 10.5 or higher, the organic solution is brought into contact with 0.1 to 2 times by volume of the alkali solution, preferably, in a non-oxidative atmosphere of nitrogen or an inert gas to prevent contacting with the atmospheric oxygen. The aqueous alkali solution is prepared by dissolving an alkali metal hydroxide, e.g. sodium hydroxide or potassium hydroxide or an alkaline earth hydroxide in water. At any rate, the aqueous alkaline extractant solution must have a pH of at least 10.5 or, preferably, the alkalinity of the solution should be in the range from a pH of 10.5 to a normality of 3 N of a strong alkali. By use of the alkaline aqueous extractant solution, the strongly antioxidative ingredient can be extracted with reliability. When the alkalinity of the extractant solution is lower than above, no satisfactory effect of extraction can be obtained.

Whereas the extraction from the organic solution with a weakly alkaline aqueous solution such as a saturated aqueous solution of sodium hydrogencarbonate cannot result in the extraction of the desired strongly antioxidative fraction, it is preferable that the extraction with the strong alkali solution is preceded by the extraction with the weak alkali solution because this pretreatment with the weak alkali solution eliminates the strongly acidic materials from the organic solution containing the solid material obtained by the solvent extraction and steam distillation from the raw starting material so that the efficiency of the extraction with the strong alkali solution is further improved due to the absence of the undesired strongly acidic fraction having been transferred into the weak alkali solution. Thus, it is a recommendable way to undertake an extraction procedure with a weakly alkaline aqueous solution at a pH of below 10.5 prior to the extraction with the strongly alkaline aqueous solution at a pH of at least 10.5.

The aqeous extract solution obtained by the extraction with the strongly alkaline solution contains the objective antioxidative ingredient as dissolved therein and may be used as such as an antioxidant if the alkalinity of the solution causes no problems in the foodstuffs or other materials admixed therewith. It is, however, usually preferable that the aqueous solution is used after neutralization with an acid. Alternatively, it is more preferable that, as is mentioned before, the effective ingredient is used for the antioxidizing purpose as isolated from the aqueous alkaline solution by extraction with an organic solvent following the neutralization or acidification of the solution with an acid and followed by the removal of the organic solvent by evaporation.

Further investigations by the inventors undertaken for identifying the effective antioxidative ingredient in the weakly acidic fraction prepared in the above described manner have led to establish that the effective ingredient is a novel compound named 7$\beta$,11,12-trihydroxy-6-10-(epoxymethano)abieta-8,11,13-trien-20-one (hereinafter referred to as rosmanol) expressed by the structural formula (III) given above and that the weakly acidic fraction contains 1 to 10% by weight of this effective ingredient giving rise to the unexpectedly strong antioxidative effect of the fraction.

Following is a description of the procedure to obtain rosmanol from the weakly acidic fraction in the form of the extracted material from the alkaline solution by the solvent extraction following neutralization or acidification by the techniques of column chromatography with a silica gel as the adsorbent.

Thus, the extract solution is subjected to column chromatography in which the weakly acidic extracted material contained therein is adsorbed on a silica gel adsorbent in a column and eluted with a development solution which is a solvent mixture of benzene and acetone in a ratio of 90:10 by volume to give 110 fractions of the eluate of which the 16th to 60th fractions are taken. The 16th to 38th fractions contain carnosol known to be effective as an antioxidant component and the desired rosmanol can be obtained succeeding it. The solid material obtained from the solution of the 16th to 28th fractions by removing the solvents is recrystallized from benzene to give the carnosol and a mother liquor.

The solid materials obtained from the above mentioned mother liquor of benzene and from the solution of the 29th to 38th fractions are combined together and subjected to a second column-chromatographic separation on a silica gel as the adsorbent and with the same development solution as in the first column chromatography as the eluant. The eluate solution is fractionated into 15 fractions. Carnosol is obtained from the 7th and 8th fractions in this second column chromatography and the desired rosmanol is obtained from the 10th and 11th fractions when the solid residue after evaporation of the solvents from the solution is recrystallized from acetone. Further, rosmanol can be obtained from the 39th to 60th fractions of the first column chromatography by recrystallizing the solid residue left after evaporation first from benzene and then from acetone. In addition, the mother liquor of benzene in the above recrystallization still contains the objective compound so that the solution is evaporated to dryness and the solid material left there is again subjected to a third column chromatography by use of the silica gel as the adsorbent and the same solvent mixture as used in the first and the second of the column chromatography as the development solution where the eluate solution is fractionated into 6 fractions of which the 4th fraction is evaporated to dryness followed by the recrystallization of the solid residue from acetone to give the objective rosmanol.

The characteristics and the antioxidative activity of this rosmanol are given later in the examples and, as is understood therefrom, the antioxidative effect of the compound is about twice as high as that of the carnosol which is a known antioxidant. The compound is also tasteless and odorless so that it is very suitable to prevent oxidation of various organic materials or, in particular, foodstuffs. Therefore, the antioxidant of the present invention prepared from rosemary and containing rosmanol as a novel compound is useful as an antioxidative additive in various kinds of foodstuffs such as fats and oils of animal and vegetable origins including fish oils, lard, tallow, beef fat, chicken oil, soybean oil, linseed oil, cottonseed oil, safflower oil, rice oil, corn oil, coconut oil, palm oil, sesame oil, cacao butter, castor oil, peanut oil and the like and processed foodstuffs including butter, cheese, margarin, shortening, mayonnaise, salad dressings, hams, sausages, potato chips, fried crackers, fried vermicelli, curry roux, soy sauce, refreshing drinks, alcoholic drinks and wines, ketchup, jam and fish- or meat-paste products, and so on as well as cosmetic and toiletry products including hair-treatment and skin-care products and oral hygienic products and medicines susceptible to oxidation.

The amount of addition of rosmanol in the above named foodstuffs and other products is preferably in the range from 0.00005 to 0.02% by weight or, more preferably, from 0.0001 to 0.01% by weight on the base of the dry weight. It is of course that rosmanol may be used as such but it may be processed into a powdery or granular form according to need by adding a suitable vehicle or excipient such as starch, gelatin and the like. Further, the effective compound may be processed into a liquid antioxidant composition by dissolving or dispersing in a suitable liquid such as oils, ethyl clcohol, propyleneglycol, glycerin and the like or a mixture thereof. It is sometimes effective that the inventive antioxidant contains a synergistic ingredient such as citric acid and the like or rosmanol is combined with a synergistic ingredient.

The inventive antioxidant is a product obtained from a natural plant or, in particular, from rosemary so that it is quite free from the problem of safety and tastiness when it is used by adding in foodstuffs, in particular, in oleaginous foodstuffs, cosmetic and toiletry products and medicines and a great advantage is obtained by the use thereof in contrast to the synthetic antioxidants.

Following are the examples in detail to illustrate the preparation of the inventive antioxidant, the antioxidative effect of the inventive antioxidant and isolation and characterization of rosmanol contained therein.

EXAMPLE 1

Extraction of 500 g of dried and pulverized leaves of rosemary was performed by adding 1.2 liters of n-hexane thereto and agitating the mixture overnight at room temperature followed by filtration with suction to collect the undissolved solid material. Extraction was repeated three times with the solid material from the preceding extraction each time by use of the same volume of n-hexane as the extractant. The extract solutions obtained in these three times of extraction were combined together and the solvent was removed therefrom by distillation under reduced pressure to give 19.71 g of a concentrate extracted with n-hexane.

In the next place, 19.71 g of the above obtained concentrate were dispersed in 200 ml of water and subjected to steam distillation to remove 2.75 g of a volatilizable matter. The aqueous dispersion after the steam distillation was filtered and separated into the filtrate and the solid material.

The solid material obtained in the above was dissolved in 400 ml of diethyl ether and the ether solution was twice extracted each time with 150 ml of a 2 N hydrochloric acid. The ether solution separated from the aqueous phase of the hydrochloric acid was, after washing twice with water, then extracted three times each time with 150 ml of a saturated aqueous solution of sodium hydrogencarbonate under a stream of nitrogen gas. The ether solution separated from the saturated aqueous solution of sodium hydrogencarbonate was, after washing twice with water, extracted in a similar manner four times each time with 150 ml of a 1 N aqueous solution of sodium hydroxide under a stream of nitrogen gas and the aqueous alkali solution was separated from the ether solution.

The ether solution was further washed twice with water and, after drying with anhydrous magnesium sulfate, concentrated to dryness to give 10.2 g of a neutral fraction. On the other hand, the acidic aqueous solution obtained in the extraction above with a 2 N hydrochloric acid was made alkaline by adding a 4 N aqueous solution of sodium hydroxide followed by extraction with diethyl ether and the ether solution was evaporated to dryness to give only a trace amount of the basic fraction. The aqueous extract solution obtained in the extraction with the saturated solution of sodium hydrogencarbonate was made acidic by adding a 4 N hydrochloric acid followed by extraction with diethyl ether and the ether solution was washed with water, dehydrated and evaporated to dryness to give 0.049 g of the strongly acidic fraction.

Similarly, the aqueous extract solution obtained in the extraction with the aqueous solution of sodium hydroxide was acidified by adding 4 n hydrochloric acid followed by extraction with diethyl ether and the ether solution was washed with water, dehydrated and evaporated to dryness to give 1.9 g of the weakly acidic fraction which was the inventive antioxidant. The results of the analysis undertaken with this fraction indicated that the content of rosmanol therein was about 3.2%.

For comparison, the distillate obtained in the steam distillation of the extract of rosemary with n-hexane was subjected to the same column chromatographic treatment as above and a neutral and a weakly acidic fractions were obtained.

The antioxidative activity of the above prepared fractions was evaluated according to the testing procedure of AOM method described in Yukagaku (Oil Chemistry), volume 19, No. 5, page 62 by adding 0.01% by weight of each of the tested fractions to lard and by determining the peroxide value (POV) to give the results shown in Table 1 and FIG. 1.

TABLE 1

| Test No. | Fraction of antioxidant | | 12 | 14 | 16 | 18 | 20 | 22 | 24 |
|---|---|---|---|---|---|---|---|---|---|
| | | | \multicolumn{7}{c}{(Peroxide value, meq/kg lard) Testing time in AOM method, hours} | | | | | | |
| 1 | None | | 23.5 | 207 | — | — | — | — | — |
| 2 | Distilled out in the steam distillation of n-hexane extract | neutral | 19.7 | 153 | 370 | — | — | — | — |
| 3 | | weakly acidic | 19.5 | 164 | 332 | — | — | — | — |
| 4 | Not distilled out in the steam distillation of n-hexane extract | neutral | 18.3 | 28.1 | 58.2 | 161 | — | — | — |
| 5 | | weakly acidic | 0.5 | 1.3 | 2.0 | 2.6 | 5.7 | 10.2 | 14.3 |
| 6 | | strongly acidic | 20.7 | 37.6 | 253 | — | — | — | — |

The curves I to VI in FIG. 1 each correspond to the data in the Test Nos. 1 to 6 in Table 1, respectively. Further, the curve Va is plotted with the data obtained by use of the same antioxidant fraction as in the curve V but by decreasing the amount of the antioxidant to 0.005% by weight instead of 0.01%.

As is understood from the results shown in Table 1 and FIG. 1, the wealky acidic fraction, i.e. only the fraction obtained according to the inventive method has an outstandingly high antioxidative power.

EXAMPLE 2

A 1.42 g portion of the weakly acidic fraction obtained in Example 1 was subjected to the column chromatography by the adsorption on 80 g of the silica gel contained in a column of 3.0 cm inner diameter and 24 cm length and elution with a development solution which was a 90:10 by volume mixture of benzene and acetone at a rate of 0.5 ml/minute. The eluate solution was fractionated into 110 fractions of each 10 ml volume and the 16th to 60th fractions were taken and each evaporated to dryness to give the respective solid materials. The solid materials obtained from the 16th to 28th fractions, weighing 348 mg as a total, were dissolved together in 3 ml of benzene and recrystallized therefrom to give 180 mg of a colorless, needle-like crystals melting at 233° C. This crystalline material was identified to be carnosol from the results of the instrumental analyses undertaken therewith.

The solid residue obtained by evaporating the benzene from the above mother liquor from which the crystals of carnosol had been removed was combined with 108 mg of the solid materials from the 29th to 38th fractions and 274 mg of the thus combined solid materials were subjected to a second column chromatography by the adsorption on 20 g of the silica gel in a column of 2.0 cm inner diameter and 17 cm length and elution with the same development solution as in the first column chromatography at a rate of 0.5 ml/minute. The eluate solution was fractionated into 15 fractions of each 10 ml volume and the 7th and 8th fractions were taken and evaporated to dryness to give a solid material which was recrystallized from benzene to give 120 mg of carnosol. Similarly, the 10th and 11th fractions were evaporated to dryness to give a solid material which was recrystallized from acetone to give 26 mg of a crystalline material.

Separately, on the other hand, the 39th to 60th fractions obtained in the first column chromatography were combined together and evaporated to dryness to give a solid material and 107 mg of this solid material were dissolved in 1 ml of benzene and recrystallized therefrom to be separated into the crystalline material insoluble in benzene and the portion soluble in benzene and contained in the mother liquor of the recrystallization. The crystalline material was further recrystallized from acetone to give 10 mg of a crystalline product.

The benzene solution as the mother liquor in the above recrystallization was evaporated to dryness and 80 mg of the solid material left there were subjected to a third column chromatography by the adsorption on 8 g of the silica gel in a column of 1.5 cm inner diameter and 11 cm length and elution with the same development solution as used in the first and the second of the column chromatography at a rate of 0.35 ml/minute. The eluate solution was fractionated into 6 fractions of each 7 ml volume and the 4th fraction was evaporated to dryness to give a solid material which was recrystallized from acetone to give 10 mg of a crystalline product.

The crystalline products prepared from the 10th and 11th fractions of the second column chromatography, from the 39th to 60th fractions of the first column chromatography and from the 4th fraction of the third column chromatography were found to be the same compound and identified to be a compound expressed by the structural formula (III) and named here as rosmanol from the results of the analyses shown below.

Appearance: colorless, prismatic crystals.
Melting point: 241° C.
$\lambda_{max}$, of ultraviolet absorption in ethyl alcohol solution (log $\epsilon$): 209 nm (4.49); 226 nm (S) (4.28); 282 nm (3.45)
Specific rotatory power: $[\alpha]_D^{18} = -34.3°$

| | Found, % | Calculated for $C_{20}H_{26}O_5$, % |
|---|---|---|
| C | 69.63 | 69.34 |
| H | 7.63 | 7.57 |

Figure 2:
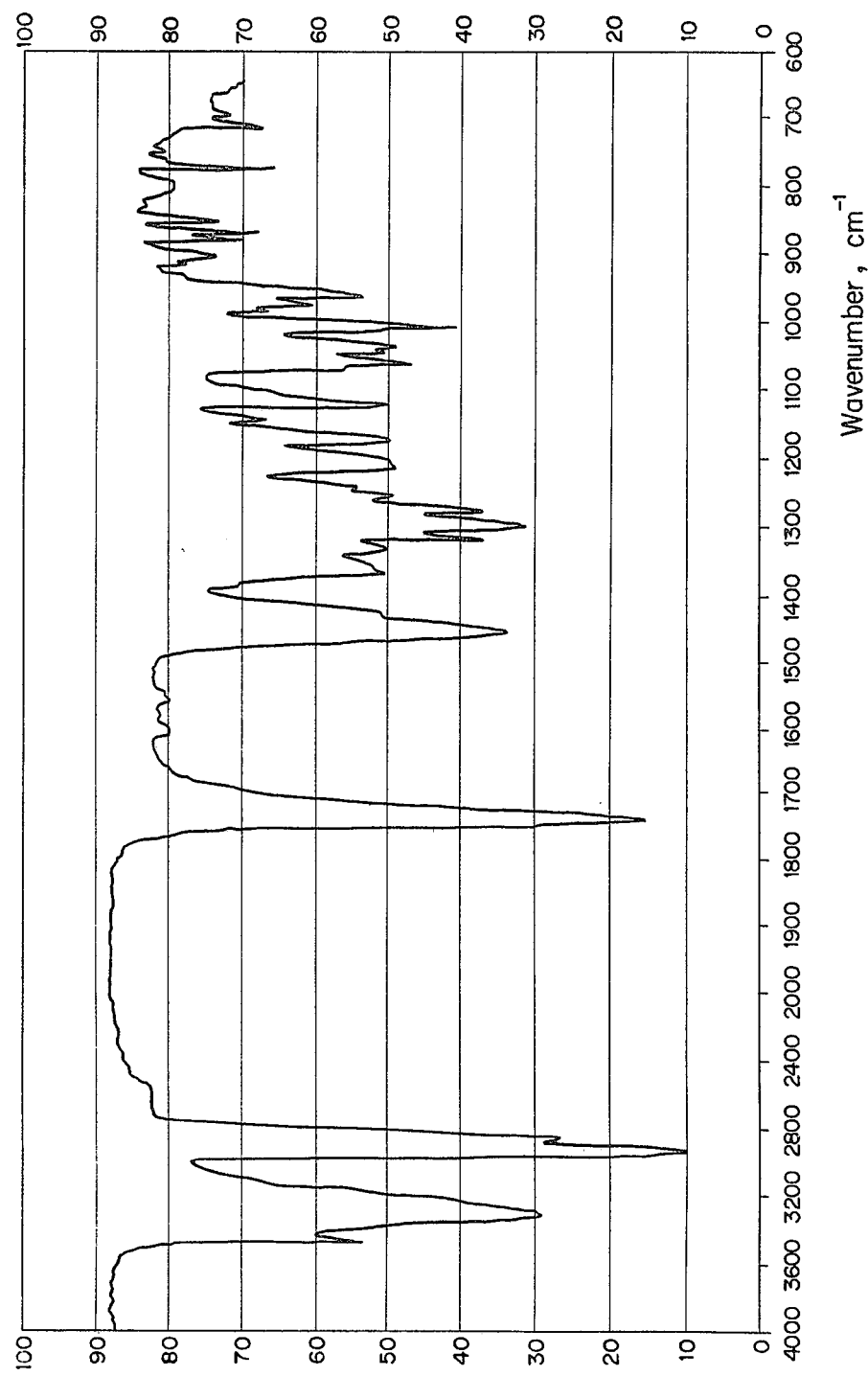
FIGS. 2, 3 and 4 are the infrared absorption spectrum, NMR absorption spectrum and mass spectrum, respectively, of the compound 7β,11,12-trihydroxy-6,10-(epoxymethano)abieta-8,11,13-trien-20-one.

$\nu_{max}$, cm$^{-1}$, of infrared absorption in nujol mull: 3500; 3320; 1740; 1320; 1300; 1280; 1005 (see FIG. 2).

Figure 3:
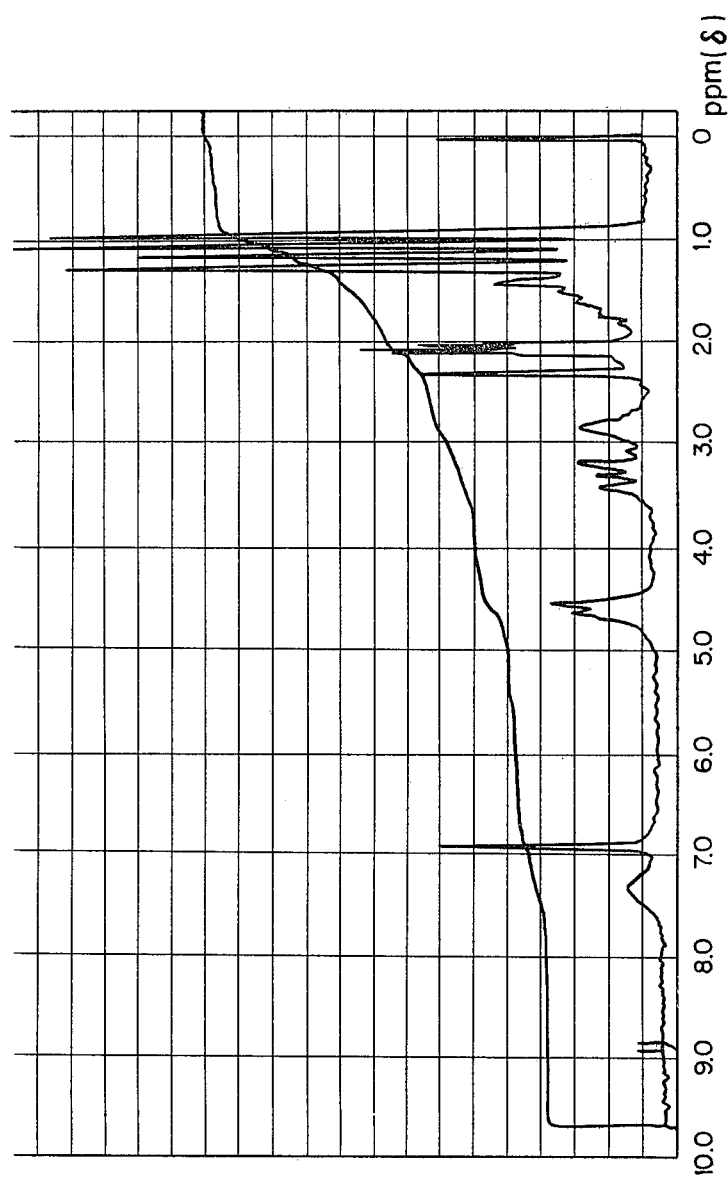

NMR (d$_6$-acetone) ($\delta$): 0.90 (3H, S); 1.02 (3H, S); 1.17 (6H, d, J=7.2 Hz); 1.2–2.0 (5H); 2.29 (1H, S); 3.0–3.5 (2H); 4.4–4.7 (2H); 6.90 (1H, S); 7.3 (2H, br, S) (see FIG. 3).

Figure 4:
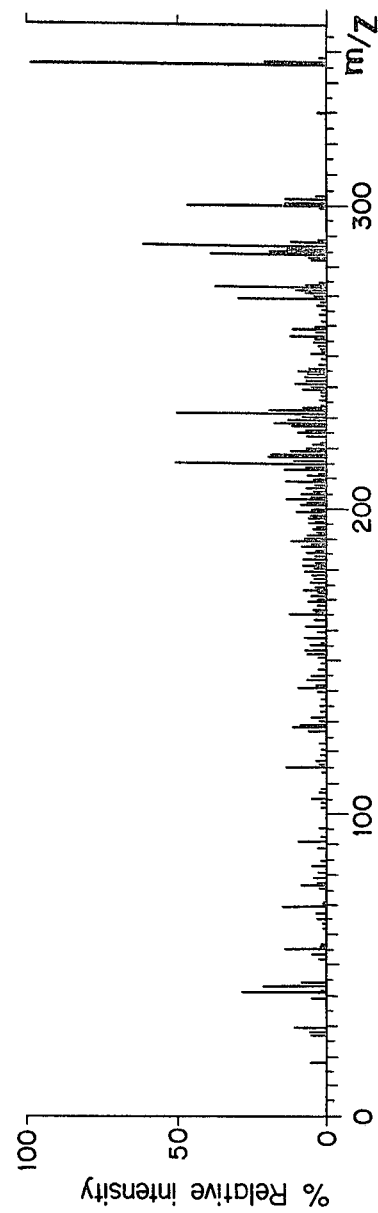

Mass spectrometry, m/Z, (%) (energy of electrons 70 eV; accelerating voltage 3.5 kV): 346 (M+, 100); 300 (48); 287 (62); 284 (41); 273 (38); 269 (31); 231 (51); 215 (51) (see FIG. 4).

Figure 5:
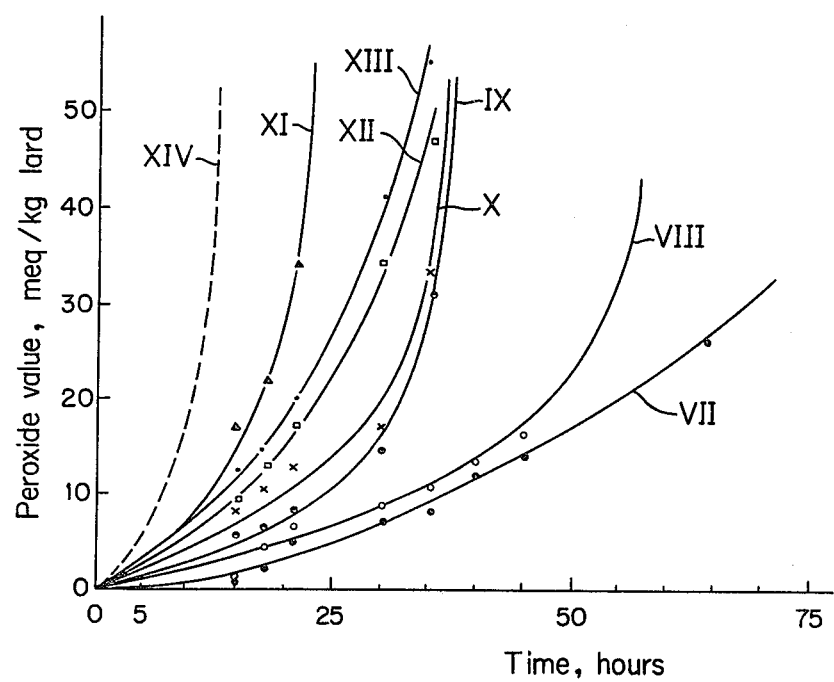
FIG. 5 is a graph showing the antioxidative effect of the above compound and several other antioxidative compounds. See text for the Nos. VIII to XIV indicating the curves.

In the next place, comparative tests were undertaken for the anitioxidative effects of the above obtained rosmanol, carnosol and α-tocopherol as the natural-origin antioxidants as well as BHA and BHT as the synthetic antioxidants according to the AOM method. Control test was performed with lard containing no antioxidant. The peroxide values of the lard samples were determined without or with addition of either one of the above named antioxidant compounds in an amount as shown in Table 2 below which summarizes the results of the determination of the peroxide values. The results are also shown graphically in FIG. 5, in which the curves VII to XIV each correspond to the data of the Test Nos. 7 to 14, respectively.

TABLE 2

| Test No. | Antioxidant compound (% by weight addition in lard) | (Peroxide value, meq/kg lard) Testing time in AOM method, hours | | | | | | | |
|---|---|---|---|---|---|---|---|---|---|
| | | 15 | 18 | 21 | 30 | 35 | 40 | 45 | 64 |
| 7 | Rosmanol (0.02) | 0.97 | 2.37 | 5.12 | 7.54 | 8.14 | 12.11 | 14.20 | 25.91 |
| 8 | Rosmanol (0.01) | 1.01 | 4.72 | 6.65 | 9.17 | 10.88 | 13.54 | 16.47 | 429 |
| 9 | Rosmanol (0.005) | 5.91 | 6.63 | 8.57 | 14.32 | 30.83 | 277 | — | — |
| 10 | Carnosol (0.01) | 8.56 | 10.73 | 12.87 | 16.93 | 33.48 | 383 | — | — |
| 11 | α-Tocopherol (0.02) | 17.3 | 22.4 | 34.5 | 282 | — | — | — | — |
| 12 | BHA (0.02) | 9.2 | 13.3 | 17.4 | 34.5 | 46.8 | 63.4 | 117 | — |
| 13 | BHT (0.02) | 12.6 | 14.7 | 20.3 | 40.8 | 55.2 | 77.2 | 182 | — |
| 14 | None | 243 | — | — | — | — | — | — | — |

What is claimed is:

1. A method for the preparation of an antioxidant for organic materials which comprises the steps of
(a) extracting rosemary with a non-polar organic solvent to give an extracted material in the solvent,
(b) subjecting the extracted material from rosemary to steam distillation to remove volatile matter and to leave a residue, and
(c) extracting the residue after the steam distillation with an aqueous alkaline solution having a pH of at least 10.5.

2. A method for the preparation of an antioxidant for organic materials which comprises the steps of
(a) subjecting rosemary to steam distillation to remove volatile matter,
(b) extracting the rosemary after the steam distillation with a non-polar organic solvent to give an extracted material in the solvent, and
(c) extracting the extracted material obtained in the step (b) above with an aqueous alkaline solution having a pH of at least 10.5.

3. The method as claimed in claim 1 or claim 2 wherein the non-polar organic solvent is selected from the group consisting of petroleum ether, ligroin, n-hexane, cyclohexane, carbon tetrachloride, chloroform, dichloromethane, dichloroethanes, monochloroethane, diethyl ether, benzene and toluene.

4. The method as claimed in claim 1 or claim 2 wherein the aqueous alkaline solution is an aqueous solution of an alkali metal hydroxide.

5. The method as claimed in claim 1 or claim 2 wherein the step (c) of the extraction with the aqueous alkaline solution having a pH of at least 10.5 is preceded by an extraction with a weakly alkaline aqueous solution having a pH below 10.5.

6. A method for preventing oxidation of an organic material which comprises admixing the organic material with 7β,11,12-trihydroxy-6,10-(epoxymethano)abieta-8,11,13-trien-20-one.

7. 7β,11,12-Trihydroxy-6,10-(epoxymethano)abieta-8,11,13-trien-20-one expressed by the following structural formula:

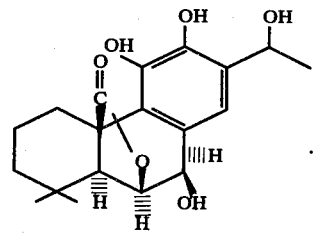

8. A method for the preparation of 7β,11,12-trihyroxy-6,10-(epoxymethano)abieta-8,11,13-trien-20-one which comprises the steps of
(a) extracting rosemary with a non-polar organic solvent to give an extracted material in the solvent,
(b) extracting the extracted material obtained in the step (a) above with an aqueous alkaline solution having a pH of at least 1.5 to give a weakly acidic fraction,
(c) subjecting the weakly acidic fraction to column chromatography.

* * * * *